Figure 1:
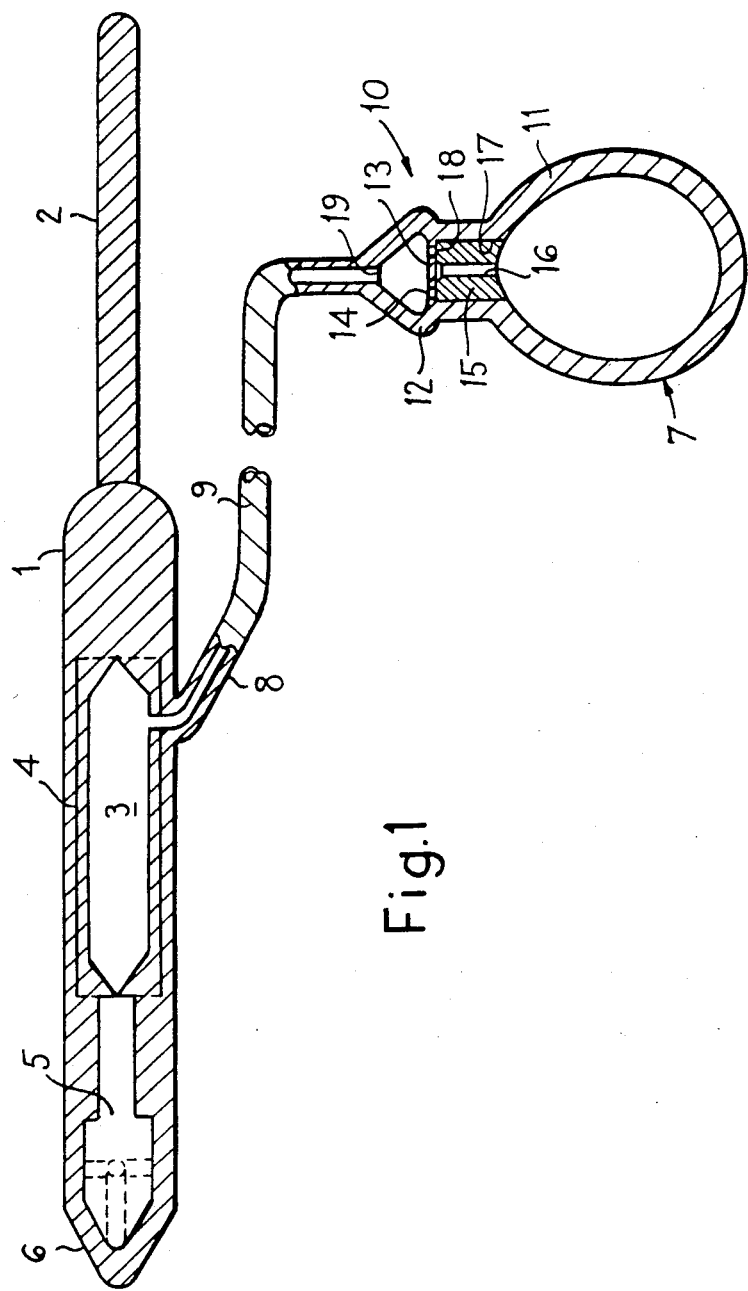

United States Patent [19]

Hakky

[11] Patent Number: 4,718,410

[45] Date of Patent: Jan. 12, 1988

[54] SURGICAL IMPLANTS

[76] Inventor: Said I. Hakky, P.O. Box 783, Baghdad, Iraq

[21] Appl. No.: 192,384

[22] PCT Filed: Aug. 2, 1979

[86] PCT No.: PCT/GB79/00130

§ 371 Date: Apr. 1, 1980

§ 102(e) Date: Apr. 1, 1980

[87] PCT Pub. No.: WO80/00302

PCT Pub. Date: Mar. 6, 1980

[30] Foreign Application Priority Data

Aug. 2, 1978 [GB] United Kingdom ............... 32037/78
Dec. 29, 1978 [GB] United Kingdom ............... 50188/78

[51] Int. Cl.$^4$ ................................................ A61F 5/00
[52] U.S. Cl. ............................................................ 128/79
[58] Field of Search .......... 128/79, 1 R, 344, DIG. 25

[56] References Cited

U.S. PATENT DOCUMENTS

| | | | |
|---|---|---|---|
| 3,853,122 | 12/1974 | Strauch et al. | 128/79 |
| 3,895,637 | 7/1975 | Choy | 128/344 X |
| 3,954,102 | 5/1976 | Buuck | 128/79 |
| 4,009,711 | 3/1977 | Uson | 128/79 |
| 4,018,230 | 4/1977 | Ochiai et al. | 128/344 |
| 4,267,829 | 5/1981 | Burton et al. | 128/79 |

Primary Examiner—Dalton L. Truluck
Attorney, Agent, or Firm—Caesar, Rivise, Bernstein, Cohen & Pokotilow, Ltd.

[57] ABSTRACT

A penile implant for assisting disabled men to achieve satisfactory sexual intercourse comprises a flexible rod-like body (1) having an inflatable chamber (3) surrounded by a non-stretchable mesh (4), and a flexible tail portion (2) projecting from the proximal end of the body. A flexible tube (8) connects the chamber to a flexible bulb (7) for pressurizing the chamber, this tube and bulb also being implantable in the patient's body. A non-return valve (10) at the outlet of the bulb prevents return of pressure fluid to the bulb when the chamber is pressurized to stiffen the implant. The valve housing (12) is integral with the bulb wall (11) and can be manually distorted to release the pressure when the implant is to be relaxed. The chamber (3), tube (8) and bulb (7) are filled with fluid at atmospheric pressure. In a modification, the inflatable chamber is constructed so as to be axially expandible upon inflation thereof so as to produce a more natural physiological action.

19 Claims, 2 Drawing Figures

SURGICAL IMPLANTS

The present invention relates to surgical implants and, more particularly, to penile implants for assisting disabled men to have satisfactory sexual intercourse and achieve fertilisation of the women's ova.

In order successfully to achieve fertilisation, it is necessary for the man's penis to be erect so as to penetrate as deeply as possible into the woman's vagina. Many disabled men, such as spastics, paraplegics and those suffering from chronic leukemia, whilst capable of producing semen for the reproductive process are not capable of having an erection and, therefore, cannot satisfactorily penetrate the woman's genital canal to fertilise the ova and initiate such reproduction. This disability can be rectified by means of surgical implants. For example, in one implant procedure two inflatable members are implanted respectively in the corpora cavernosa of the penis and a reservoir containing liquid for inflating the two members is implanted in the abdomen. The members are inflated, when desired, in order to erect the penis, by means of two flexible bulbs which are implanted in the scrotum and are arranged to pump liquid from the reservoir into the members. Each of these bulbs is connected to the reservoir and its associated inflatable member by two tubes and four valves in order to pump liquid from the reservoir into the member, when required, and subsequently to return it to the reservoir after intercourse. Such an implant is complex and expensive and involves a difficult surgical operation.

It is an object of the present invention to provide an inflatable penile implant which is much simpler than the hitherto known device and is also simpler to implant in a patient.

To this end, the invention consists in penile implant comprising a flexible rod-like body made from synthetic material and having an inflatable chamber therein, a flexible tail-like portion projecting from the proximal end of the body, a flexible bulb for containing fluid for pressurising the chamber connected to the chamber by a flexible tube, and a non-return valve arranged to prevent fluid discharged from the bulb into the chamber from returning to the bulb, said valve having a deformable housing whereby the valve can be manually distorted so as to permit the fluid to return from the chamber to the bulb.

Two implants according to the invention are used for each patient. One of the rod-like bodies is inserted into each corpora cavernosa of the penis with the tail-like portion projecting towards the base or root of the penis. This tail-like portion improves the support for the body and its affect, upon inflation of the fluid chamber. The body is inserted into the penis through a small incision made in the underside. The associated bulb is implanted in the dartos pouch of the scrotum and the tube connecting the bulb to the fluid chamber in the rod-like body is also suitably implanted in the patient's body so that there is no visible evidence of the implant. When the patient requires to use his implants, it is a simple matter for him to squeeze the bulbs so as to inflate and pressurise or stiffen the chambers in the rodlike bodies and erect the penis. When sexual activity is finished, it is also a simple matter for the patient to locate and deform the valve housings so as to allow the chambers to be depressurised and permit the penis to return to normal.

The fluid for inflating and pressurising the chamber in the rod-like body is charged into the chamber, tube and bulb at atmospheric pressure and may be a gas or liquid. If a liquid is utilised, this should preferably be decanted to render it gas free before it is charged into the implant.

In one embodiment, the inflatable chamber is an elongated, generally cylindrical chamber and is disposed adjacent the proximal end of the rod-like body. Reinforcing means, such as a net or mesh is embedded in the body about the chamber so as substantially to prevent the body from expanding when the chamber is pressurised in order to stiffen the implant. A reinforcing member may be embedded in the rod-like body adjacent its distal end in order to stiffen this end.

In a second embodiment, which has a physiological action more nearly resembling that occurring naturally, the inflatable chamber is constructed so as to be axially extensible or expandible upon inflation of the chamber by squeezing of the flexible bulb. Such an inflatable chamber may be defined by an elongated generally cylindrical balloon which is attached at opposite ends to distal and proximal end portions of the body and which is enclosed within a tubular bellows member similarly attached and formed from non-stretchable material. This bellows member constrains the balloon to expand or contract axially when inflated or deflated. It may, itself, be enclosed within a second tubular bellows member made from resilient synthetic material and also attached at opposite ends to the distal and proximal end portions of the body. This bellows and balloon assembly may be encased within an external membrane of resilient synthetic material which is attached at opposite ends to the end portions of the body substantially flush with the adjacent peripheries thereof.

Hence, when a patient fitted with two penile implants according to this second embodiment squeezes the associated bulbs so as to inflate and pressurise the chambers, the rod-like bodies extend or expand axially of the implant so as to erect the penis. When the patient deforms the valve housings of the non-return valves so as to allow the inflatable chambers to depressurise, the bodies contract axially to permit the penis to return to normal. It will be appreciated, therefore, that these implants produce an artificial erection which, physiologically, is very similar to that occurring naturally. Moreover, this embodiment has the advantage that the size of bulb required for inflating the chamber is significantly smaller.

Preferably, the tail-like portion of the implant is solid and formed from resilient synthetic material and is inclined to the axis of the rod-like body. To improve the physiological action, the distal end of the body may be formed with means, such as grooves, which enable the tissue of the penis to key with this end of the body so that the distal end of the penis is positively moved together with the implant.

Conveniently, the non-return valve is located at the bulb outlet, with the valve housing being formed integrally with the bulb. The valve may comprise a flexible valve disc integral with the valve housing and have one or more orifices via which fluid is discharged from the bulb. The disc is resiliently urged into contact with a valve seat which closes the orifices in order to prevent return flow to the bulb. However, when it is desired to release the pressure in the inflatable chamber, the valve housing may be manually deformed so as to distort the disc out of contact with the seat and permit fluid to return to the bulb via the orifices. In an alternative construction, the valve may comprise a ball or similar floating valve member which engages a seat at the bult outlet so as to prevent return fluid flow to the bulb. As with the first mentioned construction, the valve housing may be readily deformed to unseat the valve member and permit return flow.

Figure 2:
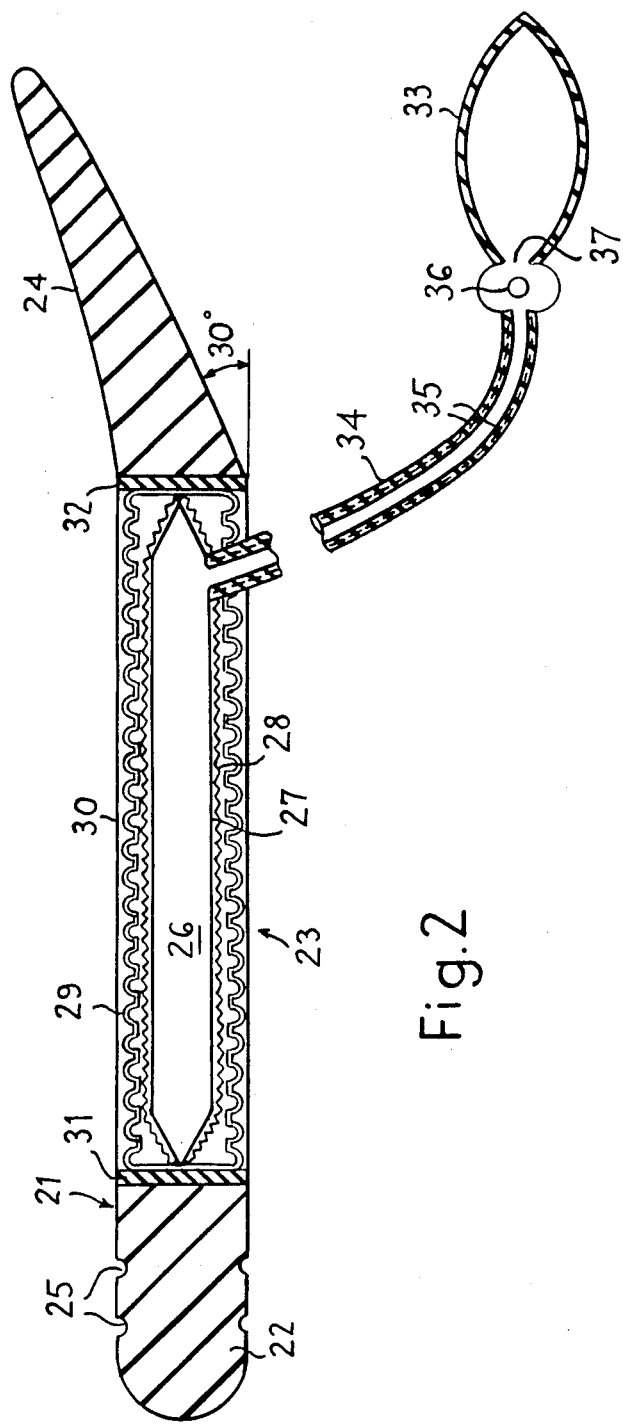

In order that the invention may be more readily understood, reference will now be made to the accompanying drawings in which FIGS. 1 and 2 illustrate sectional views through two different embodiments of the invention, respectively.

Referring to FIG. 1 of the drawings, the implant comprises a flexible rod-like body 1 moulded from a resilient synthetic material, such as silicone rubber. Moulded coaxially with the body and projecting from its proximal end is a solid, flexible, tail-like portion 2. An elongated cylindrical chamber 3 is formed within the body, coaxially therewith, adjacent its proximal end. A reinforcing net or mesh 4 of non-stretchable material, such as a Dacron mesh, is embedded in the material of the body about the chamber so as substantially to prevent the chamber from expanding when it is inflated. Embedded in the body forwardly of the chamber and extending towards the distal end of the body is a stiffening member 5. This may be moulded from polypropylene. Alternatively, the distal end portion of the body may be stiffened by injecting hard silicone rubber into this end of the body. The distal end 6 of the body is tapered to a rounded point.

The chamber 3 is connected adjacent its proximal end to a flexible bulb 7 by means of a flexible tube 8. This tube is reinforced by a spiral filament 9 of rigid plastics material which is embedded in the tube along the full length thereof. The bulb may be moulded from silicone rubber and incorporates a non-return valve 10 at its outlet. The bulb wall 11 is integral with the valve housing 12 and the valve element comprises a resilient disc 13 moulded integrally with the housing. The disc 13 has four orifices 14 (only two of which are shown in FIG. 1) equally spaced about its centre. It cooperates with a rigid valve seat member 15 which has a central passageway 16 and which is secured within a cavity 17 in the bulb on the inside of the valve disc so that the valve seat 18 at its upper end closes the orifices in the valve disc when this is in its normal position. At its other end the valve housing has a port 19 connected to the tube 8.

The chamber 3, tube 8, and bulb 7 are filled with a gas or liquid at atmospheric pressure.

Two of the foregoing implants are utilised in a patient. When they have been implanted in the manner described above, it is a simple matter for the patient to produce an erection by squeezing the bulbs which have been implanted in his dartos pouch. When each bulb is squeezed, the pressure produced in the bulb lifts the valve disc 13 off its seat 18 and allows the pressurised fluid to flow through the orifices 14 into the tube and, thence, into the chamber 3, whereupon the latter is inflated and pressurised. When the bulb is released, the fluid pressure within the chamber and tube holds the valve disc against its seat and, hence, the valve shut. When it is desired to depressurise the chamber and to terminate the erection, it is also an easy matter for the patient to squeeze the valve housing 12 so as to distort this and the valve disc and, hence, disengage the orifices 14 from the valve seat 18, whereupon the pressurised fluid can return to the bulb via the orifices and the passageway 16.

In one particular example of the implant described above, the rod-like body is 150 mm long and has a diameter of 14 mm; the tail-like portion is 60 mm long; and the diameter of the maximum circular cross section of the bulb is approximately 30 mm.

FIG. 2 illustrates a penile implant which has a more natural physiological action. It comprises a rod-like body 21 having a rounded distal end or head portion 22, a central portion 23 and a tapered tail-like portion 24 at its proximal end. The head portion 22 has annular grooves 25 which serve to key the head to the tissue of the penis. The tail portion is inclined to the axis of the body 21 at an angle of approximately 30°. The head and tail portions may be formed of solid resilient synthetic material, such as silicone rubber.

The central body portion 23 includes an inflatable chamber 26 and is constructed so as to be axially extensible or expandable upon inflation of this chamber. The chamber is defined by an elongated generally cylindrical balloon 27 made from rubber or another elastic material, and similar to a Fogartty catheter balloon. The balloon is enclosed within a first tubular bellows member 28 made from non-stretchable material which constrains the balloon to expand or contract axially when inflated or deflated. This bellows member is formed from woven arterial Dacron, such as "De Bakey" arterial Dacron. The first bellows member 28 is enclosed within a second tubular bellows member 29 and the assembly of the two bellows members and the balloon is enclosed within an external covering membrane 30 which is substantially flush with the adjacent peripheries of the head and tail portions 22,24. The membrane 30 and second bellows member 29 are formed from resilient synthetic material, such as, silicone rubber. The four members 27–30 constituting the central portion 23 are arranged coaxially and are fixed at opposite ends to end walls 31,32 bonded respectively to the head and tail portions. Intermediate their opposite ends, the central body parts 27–30 are not interconnected and are free to move independently of one another.

The cylindrical balloon 27 is connected adjacent its proximal end to a flexible bulb 33 by means of a flexible tube 34. This tube is reinforced by a spiral filament 35 of rigid plastics material, such as nylon, or stainless steel, which is embedded in the tube along the full length thereof. The bulb is of ovoid shape and may be moulded from resilient synthetic material, such as silicone rubber. It has a non-return valve, schematically indicated at 36, integral with its outlet 37. The bulb 33 and the valve 37 are of similar construction to the previous embodiment and will not therefore be further described in detail. However, this particular construction of implant enables the bulb 33 to be made smaller than that required for the implant shown in FIG. 1.

The chamber 26, tube 34 and bulb 33 are filled with gas or liquid at atmospheric pressure.

As with the previous embodiment, two implants 21 are utilised for each patient. They are implanted and operated in a similar manner to that described above. When each bulb is squeezed, the pressure produced by the bulb forces liquid through the non-return valve 36 into the associated chamber 26, whereupon the latter is inflated and, owing to the constraining action of the first tubular bellows member 8, expands axially to erect the penis. When each bulb is released, its valve 36 prevents the pressurised fluid from returning from the chamber 26 to the bulb. When it is desired to depressurise each chamber and terminate the erection, it is also an easy matter for the patient to squeeze the housing of each valve so as to distort this and permit pressure fluid to return to the valve.

In one particular example of the implant shown in FIG. 2, the chamber 26 may be expanded to 10 cm in length, when inflated, whilst it contracts to 5 or 6 cm when deflated.

The annular grooves 25 about the head 22 of the body key with the penis tissue so as to cause the distal end of the penis to move with the implant when the central body portion 23 contracts upon deflation of the chamber 26. On the other hand, the outer surface of the covering membrane 30 is smooth so that this can move relatively to the penis tissue. The result is that the physiological action of the implant is substantially equivalent to that occurring naturally.

Whilst a particular embodiment has been described, it will be understood that modifications can be made without departing from the scope of the invention as defined by the appended claims.

I claim:

1. A surgical implant comprising an inflatable penile member arranged for implanting within a penis, inflating means arranged for implanting in the patient's body for inflating the penile member, said penile member comprising a flexible rod-like body formed of a synthetic material and having an inflatable chamber therein and a flexible tail-like portion projecting from the proximal end of said body, said inflatable chamber being elongated and generally cylindrical, said chamber being disposed adjacent to the proximal end of the rod-like body and surrounded by generally cylindrical means for constraining said chamber, said inflating means comprising a flexible bulb containing fluid for pressurizing and inflating said chamber and connected to said chamber by a flexible tube and a non-return valve arranged to prevent fluid discharged from the bulb into the chamber from returning to the bulb when said chamber is inflated, said constraining means comprising reinforcing means embedded in said body adjacent the distal end thereof in order to stiffen said body while substantially preventing said body from expanding radially when said chamber is inflated, said valve having manually operable means arranged to be manually operated to permit fluid to return from said chamber to said bulb.

2. The implant of claim 1 wherein said reinforcing means comprises a mesh sleeve formed of a non-stretchable material.

3. The implant of claim 2 wherein said manually operable means is arranged to be distorted to permit the return of said fluid.

4. A surgical implant comprising an inflatable penile member arranged for implanting within a penis, inflating means arranged for implanting in the patient's body for inflating the penile member, said penile member comprising a flexible rod-like body formed of a synthetic material and having an inflatable chamber therein and a flexible tail-like portion projecting from the proximal end of said body, said inflatable chamber being elongated and generally cylindrical, said chamber being disposed adjacent to the proximal end of the rod-like body and surrounded by means for constraining said chamber, said inflating means comprising a flexible bulb containing fluid for pressurizing and inflating said chamber and connected to said chamber by a flexible tube and a non-return valve arranged to prevent fluid discharged from the bulb into the chamber from returning to the bulb when said chamber is inflated, said constraining means comprising tubular bellows means and wherein said chamber is defined by an elongated generally cylindrical balloon attached at opposite ends to the rod-like body and enclosed within said bellows means, said bellows means being similarly attached to the body, said constraining means substantially preventing said body from expanding radially to enable said body to expand axially when said chamber is inflated, to stiffen said body, said valve having manually operable means arranged to be manually operated to permit fluid to return from said chamber to said bulb.

5. The implant 4 wherein said bellows means is formed of a non-stretchable material.

6. The implant of claim 5 additionally comprising an external membrane formed of a resilient synthetic material enclosing said bellows means and said balloon and attached at opposite ends to the rod-like body substantially flush with the external periphery thereof.

7. The implant of claim 6 wherein said tail-like portion is inclined to the longitudinal axis of said rod-like body.

8. The implant of claim 7 wherein the distal end of said body includes means for keying with the tissue of the penis so that the distal end of the penis is positively movable together with the implant.

9. The implant of claim 8 wherein said external membrane is smooth so that it may move relative to the penis tissue.

10. The implant of claim 9 wherein said bulb includes an outlet at which said non-return valve is located and wherein said valve includes a housing formed integrally with said bulb.

11. The implant of claim 10 wherein said inflatable chamber, flexible bulb and interconnecting tube are charged with a fluid at substantially atmospheric pressure.

12. An implantable penile prosthesis comprising:
an elongated front portion for mounting inside the distal portion of a patient's penis, said front portion comprising a cylinder which is substantially rigid so as to impart rigidity to said penis and thus provide for satisfactory erection of said penis, when said penile prosthesis is implanted in said penis and when said penile prosthesis is placed in an erect condition;
a rear portion for mounting inside the proximal portion of said penis;
a tubular section attached to and mounted between said front portion and said rear portion, and having a collapsible tubular sheath and an internal chamber means so that said penile prosthesis assumes an erect condition when fluid pressure is supplied to said chamber means and so that penile prosthesis is allowed to assume a nonerect, bent condition when fluid pressure is allowed to release from said chamber means wherein said tubular sheath is allowed to collapse when said penile prosthesis assumes a nonerect, bent condition so that when said penile prosthesis is implanted in said penis, said penis is allowed to bend in a region within the length of said tubular section; and
a pump means actuateable to supply fluid pressure to said chamber means.

13. An implantable penile prosthesis comprising:
an elongated, substantially rigid, generally cylindrical, front portion for mounting inside the distal portion of a patient's penis;

a rear portion for mounting inside the proximal portion of said penis;

a pump means; and a tubular section attached to and mounted between said front portion and said rear portion, and having a tubular sheath defining an internal chamber means in fluid communication with said pump means, said tubular sheath being collapsible but nonstretchable, so that said penile prosthesis is actuateable between an erect and a nonerect condition by the transfer of a small volume of fluid between said pump means and said chamber means.

14. The penile prosthesis of claim 12 or claim 13 further comprising a valve means in fluid communication with said chamber means and having a first state and a second state, wherein fluid is maintained in said chamber means when said valve means is in said first state, wherein fluid is allowed to release from said chamber means when said valve means is in said second state, and wherein a user may operate said valve means so as to select between said first state and said second state.

15. The penile prosthesis of claim 12 or claim 13 wherein said section comprises a length of material which substantially resists radial stretching but which is longitudinally stretchable.

16. The penile prosthesis of claim 15 wherein said section comprises a length of circumferentially corrugated tubular material.

17. The penile prosthesis of claim 16 wherein said section comprises a woven tubular mesh and wherein said tubular mesh substantially resists radial and longitudinal stretching.

18. The penile prosthesis of claim 12 or claim 13 wherein said tubular section, when said penile prosthesis is implanted in said penis, is beneath the base of said penis so that said penis is allowed to bend at its point of protrusion from the body of said patient.

19. The penile prosthesis of claim 12 or claim 13 wherein said front portion comprises a substantially solid cylinder.

* * * * *